United States Patent [19]
Buelna et al.

[11] Patent Number: 5,653,689
[45] Date of Patent: Aug. 5, 1997

[54] INFUSION CATHETER

[75] Inventors: Terrence J. Buelna, Laguna Beach; Paul Lubock, Laguna Niguel; Wayne A. Noda, Mission Viejo, all of Calif.

[73] Assignee: Abacus Design & Development, Inc., Aliso Viejo, Calif.

[21] Appl. No.: 531,242

[22] Filed: Sep. 30, 1995

[51] Int. Cl.$^6$ .................................................. A61M 25/00
[52] U.S. Cl. .............................. 604/96; 604/104; 606/108
[58] Field of Search ............................ 604/96, 101, 104, 604/265; 606/108, 192, 194

[56] References Cited

U.S. PATENT DOCUMENTS

| | | | |
|---|---|---|---|
| 4,292,974 | 10/1981 | Fogarty et al. | |
| 4,323,071 | 4/1982 | Simpson et al. | |
| 4,406,656 | 9/1983 | Hattler et al. | 604/280 |
| 4,661,094 | 4/1987 | Simpson | 604/8 |
| 4,693,243 | 9/1987 | Buras | 128/207.15 |
| 4,762,129 | 8/1988 | Bonzel | |
| 4,775,371 | 10/1988 | Mueller, Jr. | 604/280 |
| 4,850,969 | 7/1989 | Jackson | 604/96 |
| 4,877,031 | 10/1989 | Conway et al. | |
| 4,994,033 | 2/1991 | Shockey et al. | 604/101 |
| 5,015,232 | 5/1991 | Maglinte | 604/96 |
| 5,021,044 | 6/1991 | Sharkawy | 604/53 |
| 5,041,089 | 8/1991 | Mueller et al. | 604/96 |
| 5,087,244 | 2/1992 | Wolinsky et al. | 604/53 |
| 5,087,247 | 2/1992 | Horn et al. | 604/98 |
| 5,112,305 | 5/1992 | Barath et al. | 604/96 |
| 5,257,974 | 11/1993 | Cox | 604/96 |
| 5,336,178 | 8/1994 | Kaplan et al. | 604/53 |
| 5,344,402 | 9/1994 | Crocker | 604/96 |
| 5,364,356 | 11/1994 | Hofling | 604/96 |
| 5,370,614 | 12/1994 | Amundson et al. | 604/96 |
| 5,456,667 | 10/1995 | Ham et al. | 604/107 |

OTHER PUBLICATIONS

Plante, et al., "Porous Balloon Catheters for Local Delivery: Assessment of Vascular Damage in a Rabbit Iliac Agioplasty Model", *JACC*, vol. 24, No. 3, Sep. 1994, pp. 820–824.

McKay, et al., "Treatment of Intracoronary Thrombus With Local Urokinase Infusion Using a New, Site-Specific Drug Delivery System: The Dispatch Catheter", *Catheterization and Cardiovascular Diagnosis*, 33:181–188 (1994) Wiley-Liss, Inc.

Harvey Wolinsky, "Local Delivery: Let's Keep Our Eyes on the Wall", *JACC*, vol. 24, No. 3, Sep. 1994, pp. 825–827.

(List continued on next page.)

*Primary Examiner*—Corrine M. McDermott
*Attorney, Agent, or Firm*—Klein & Szekeres, LLP

[57] ABSTRACT

An infusion catheter, for use in conjunction with a balloon dilatation catheter, comprises an elongate, flexible tube defining an infusion lumen, and an expansible infusion sleeve located near its distal end, the sleeve comprising an expansible network of spacer elements disposed between proximal and distal elastomeric sealing bands. When deployed at a treatment site in a blood vessel or other bodily passage, the elongate tube of the present invention concentrically surrounds the dilatation catheter, the infusion lumen being defined therebetween, with the infusion sleeve concentrically surrounding the balloon. The spacer elements of the expansible network create an axially-elongated, circumferential flow path or interstice between the balloon and the vessel wall when the balloon is inflated, the interstice being in fluid communication with the infusion lumen, through which a therapeutic fluid is delivered to the treatment site. In a first preferred embodiment, the infusion sleeve comprises a network of filaments that define the spacer elements, wherein the network has a substantial degree of shape memory, allowing the sleeve to return to its original shape when the balloon is deflated. The grid is permanently fixed to the proximal and distal sealing bands. In a second preferred embodiment, the sleeve comprises a perforated tube of deformable, biocompatible metal formed as a mesh or latticework that defines a network of spacer elements. The perforated tube is detachably joined to the sealing bands, so that it may be left in place as a stent after the catheter is withdrawn.

27 Claims, 6 Drawing Sheets

OTHER PUBLICATIONS

Vishva Dev, et al., "Kinetics of Drug Delivry to the Arterial Wall Via Polyurethane–Coated Removable Nitinol Statent: Comparative Study of Two Drugs", *Catherterization and Cardiovascular Diagnosis*, 34:272–278 (1995) Wiley–Liss, Inc.

Kitazume, et al., "Double Perfusion System for Coronary Angioplasty at the Origin of the Main Vessel", *Catheterization and Cardiovascular Diagnosis*, 32:278–282 (1994) Wiley–Liss, Inc.

Joseph F. Mitchel, et al., "Treatment of Acute Stent Thrombosis With Local Urokinas Therapy Using Catheter–Based, Drug Delivery Systems: A Case Report", *Catyheterization and Cardiovascular Diagnosis Diagnosis*, 34:149–154 (1995) Wiley–Liss, Inc.

Qaiser Rasheed, et al., "Local Intramural Drug Delivery Using an Infusion Balloon Following Angioplasty in Normal and Atherosclerotic Vessels", *Catheterization and Cardiovascular Diagnosis*, 31:240–245 (1994) Iley–Liss, Inc.

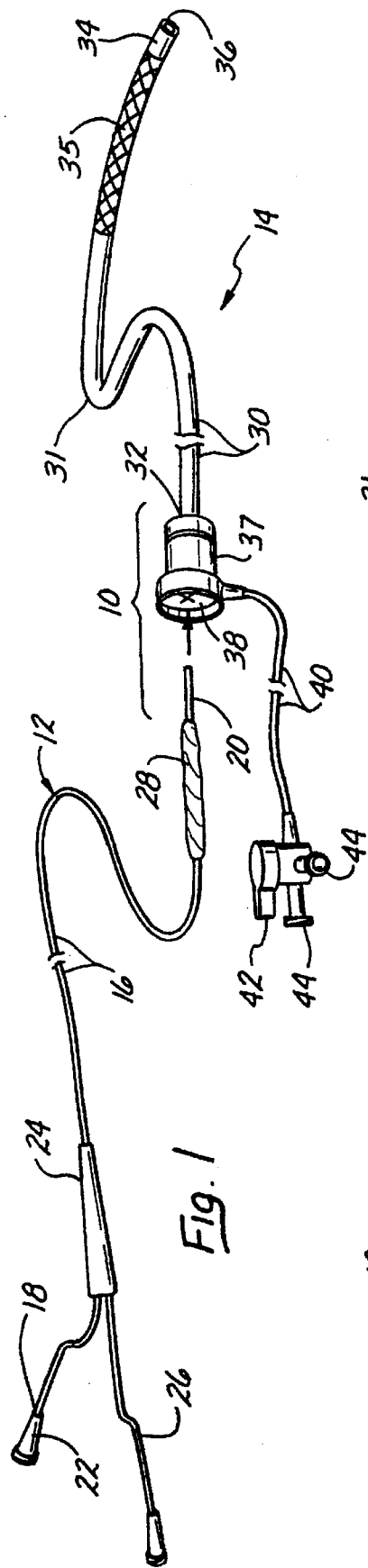
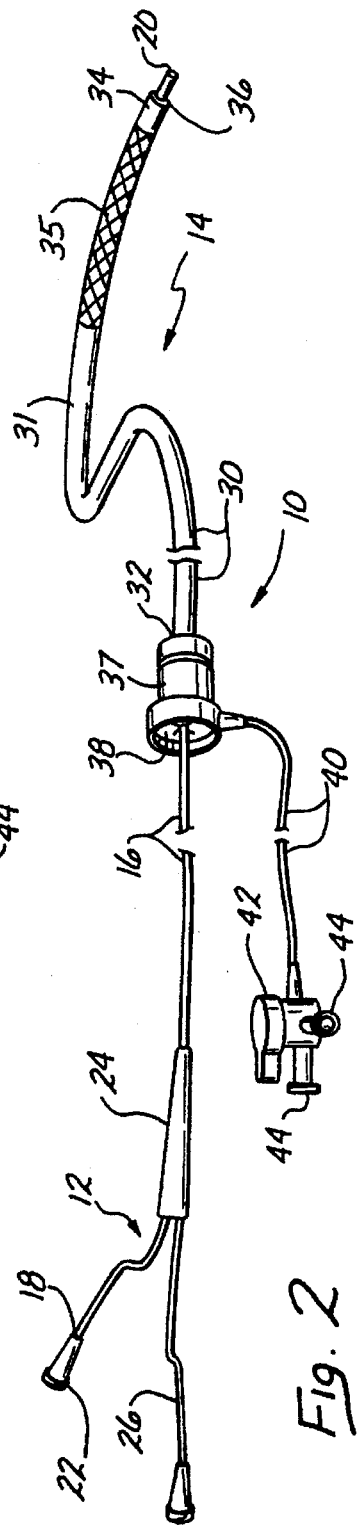
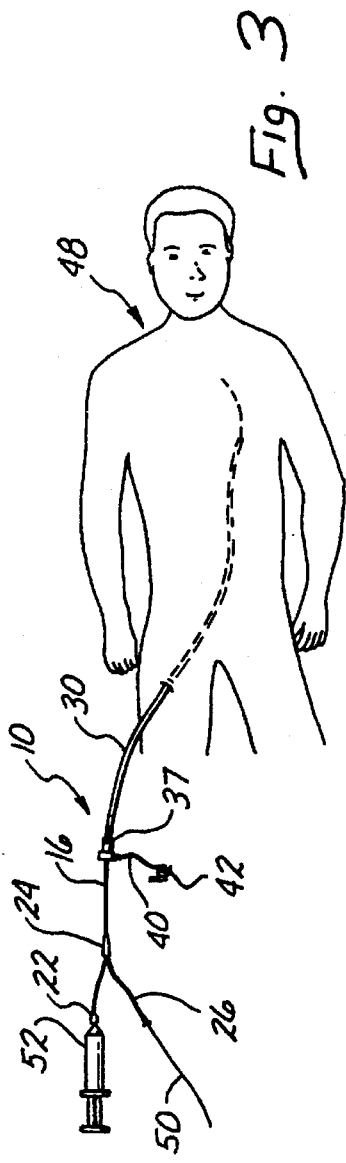

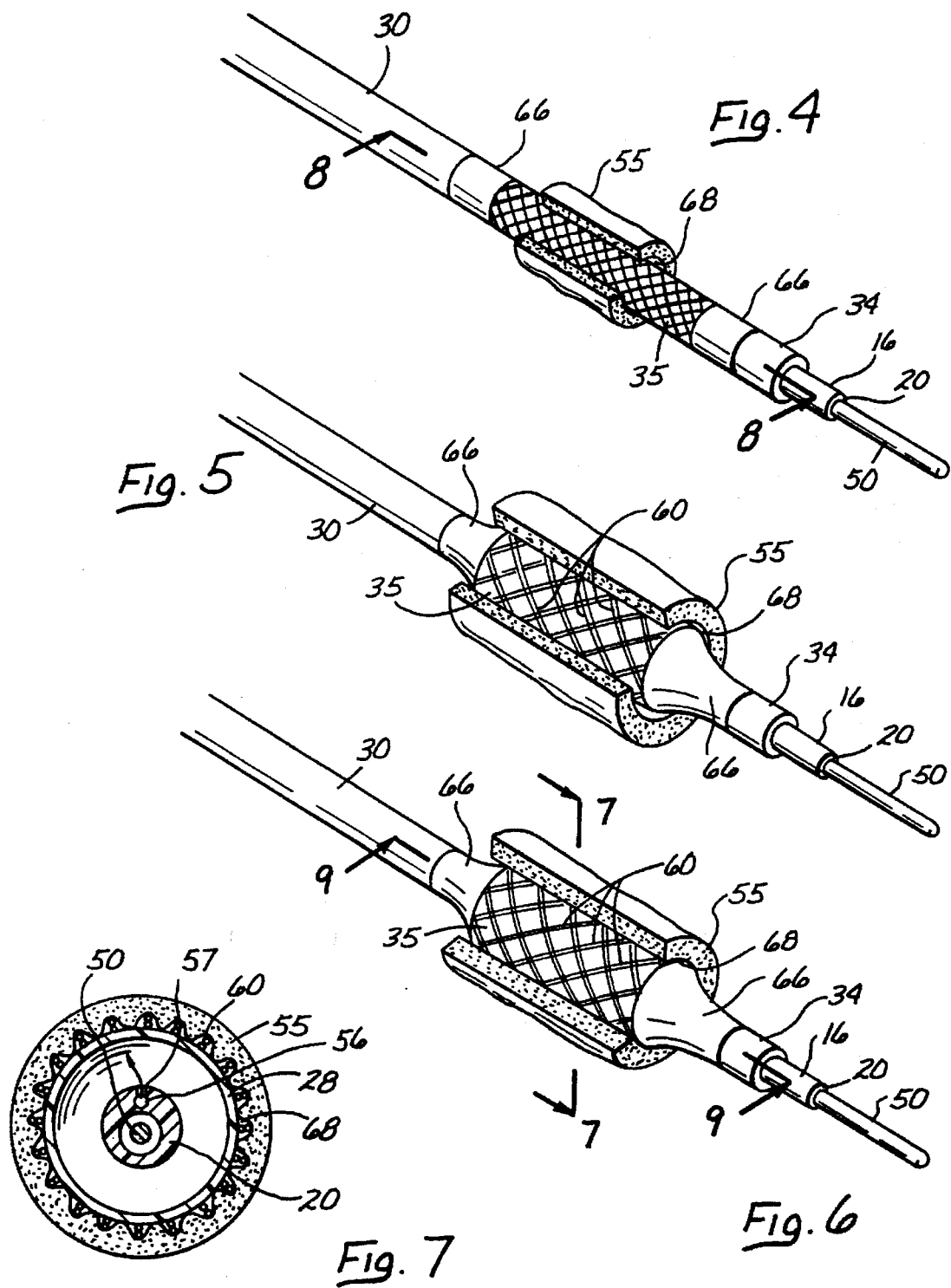

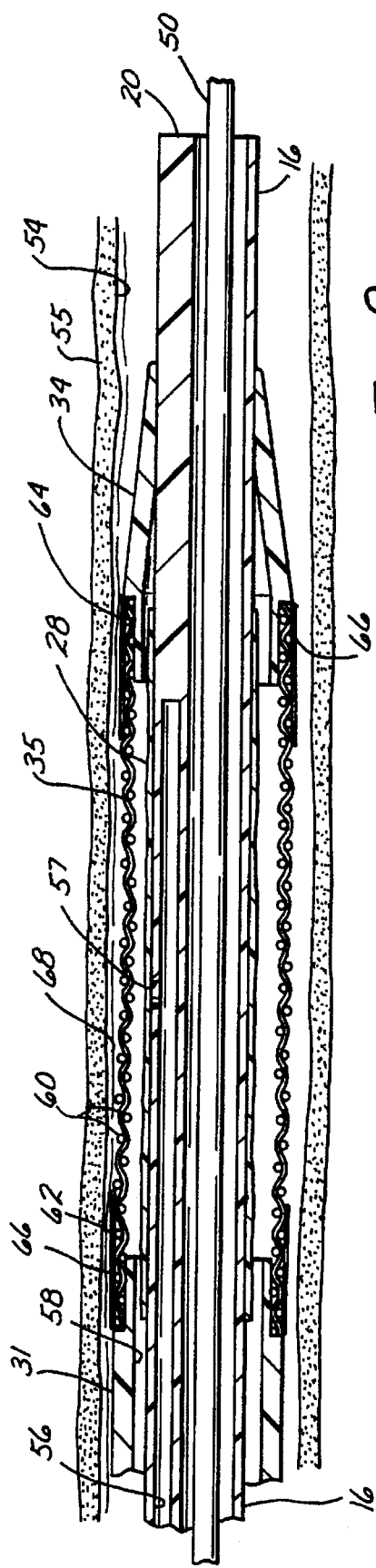
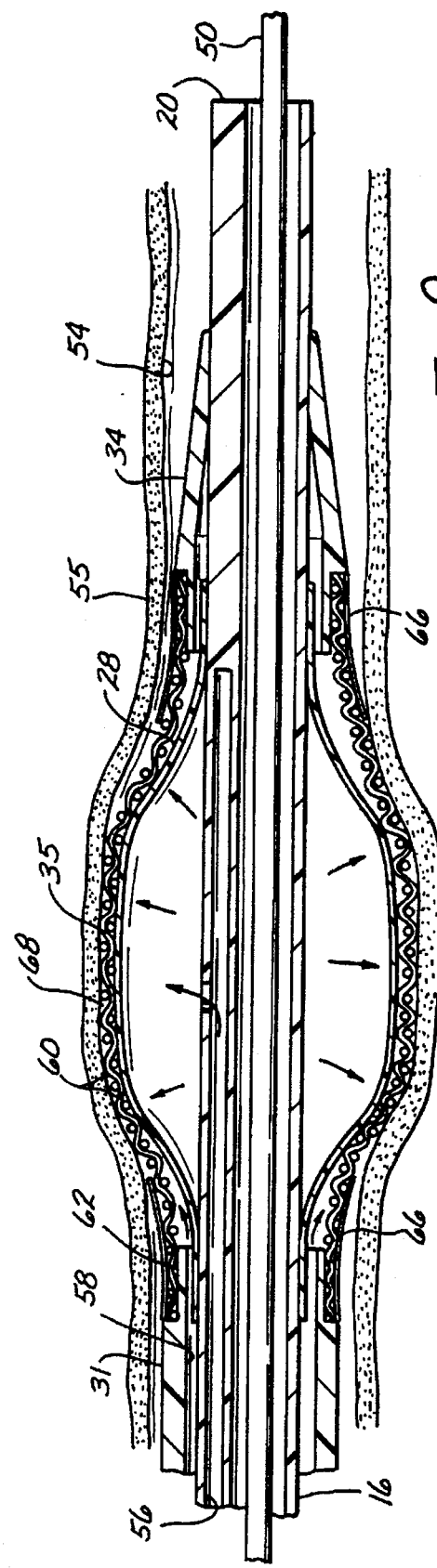

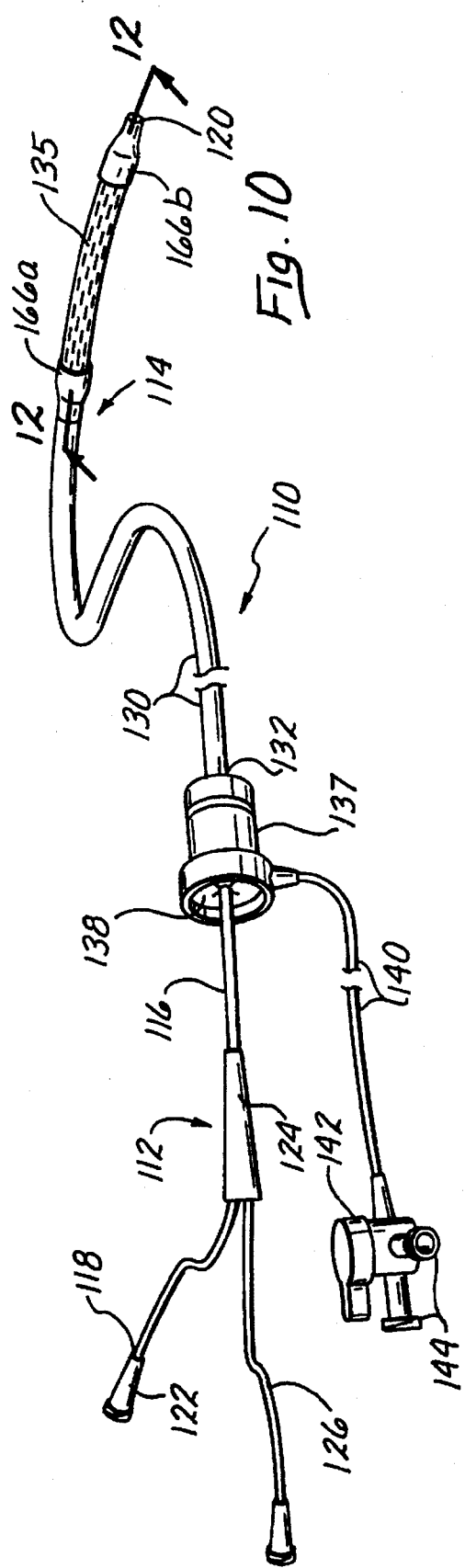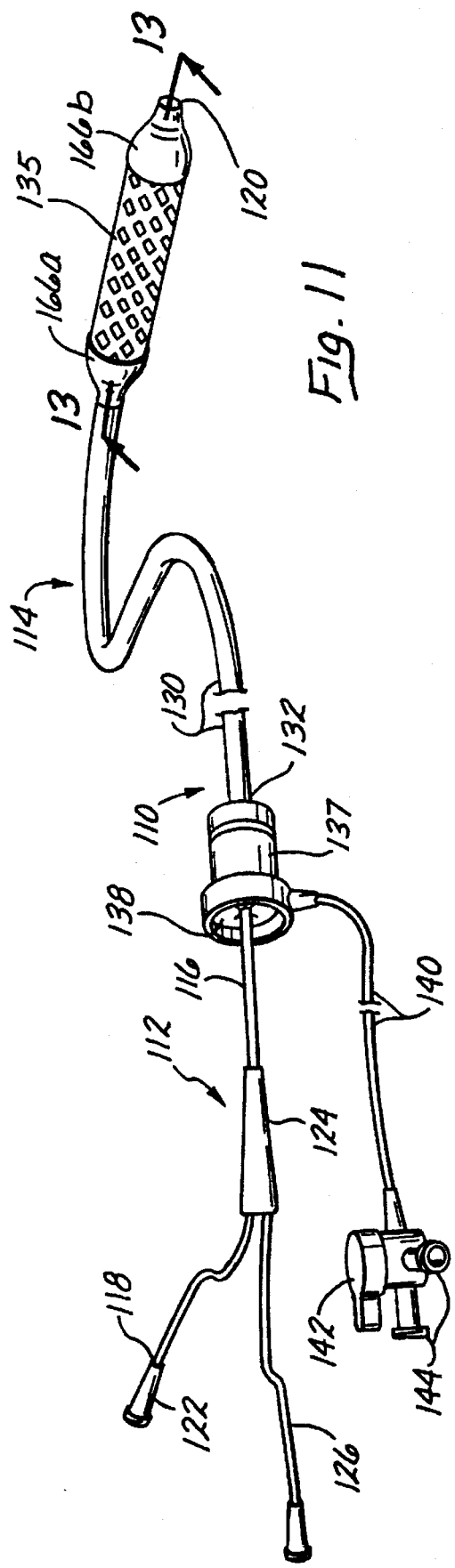

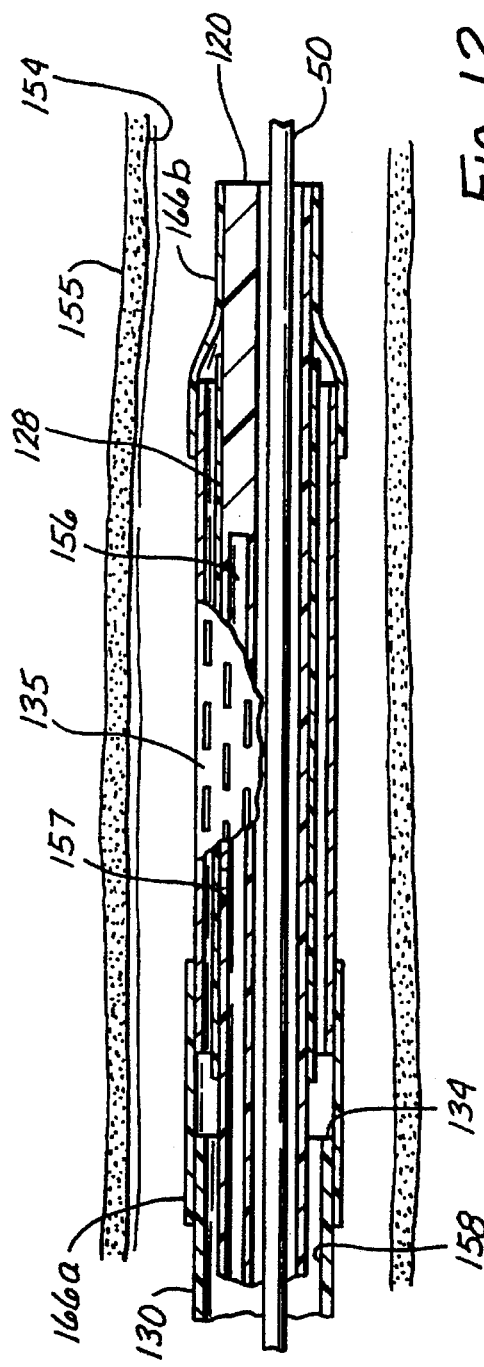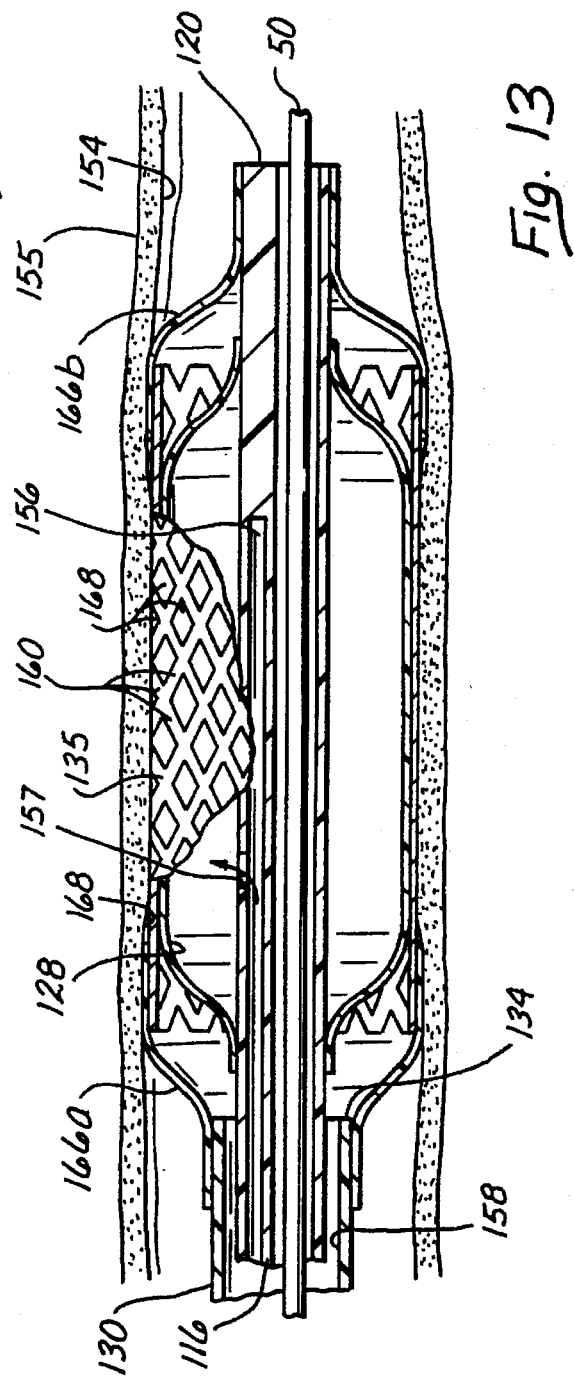

INFUSION CATHETER

BACKGROUND OF THE INVENTION

The present invention relates generally to the field of intravascular and intraluminal catheters. More specifically, it relates to a catheter that can be introduced into the lumen of a blood vessel or other bodily organ, both for the dilatation of the lumen, and for the delivery of a therapeutic agent directly to the tissues surrounding the lumen, either simultaneously or sequentially.

In the medical procedure known as percutaneous transluminal angioplasty, or PTA (sometimes called percutaneous transluminal coronary angioplasty, or PTCA), a catheter having an expansible distal end is introduced into the lumen of a blood vessel (typically a coronary artery), with the distal end positioned in the region of a previously-located stenosis. The expansible end (typically comprising an inflatable bladder or balloon) is then expanded to dilate the vessel, thereby restoring adequate blood flow through the stenotic region.

The benefits of PTA are occasionally limited by one of two mechanisms: abrupt vessel closure, and restenosis. The former is a phenomenon characterized by a rapid and acute occlusion of the vessel within the first few hours after the PTA procedure, caused principally by arterial dissection and/or thrombosis. The result frequently is myocardial infarction, with possible death, if blood flow is not quickly restored. Restenosis is the reappearance of the stenosis within a few months after the PTA procedure, requiring a repetition of the procedure. It is currently believed that the occurrence of both of these phenomena could be substantially reduced by the introduction of suitable therapeutic agents directly to the arterial wall tissue during or immediately after the PTA procedure.

The typical methods of intravascular medication involve the delivery of the medication systemically, either intravenously, or regionally (e.g., by intracoronary infusion). Systemic delivery is usually ill-suited to the treatment of conditions occurring at one or more discrete sites, because it involves the delivery of the medication to sites other than the target site, and it requires the infusion of large doses of the medication to assure the delivery of a therapeutic dose to the target site, thereby creating the possibility of deleterious effects. Thus, the dosage that can be delivered to the target site may be limited by the need to minimize unwanted effects in other parts of the body. Furthermore, systemic delivery exposes the medication to possible degradation and elimination by the action of other bodily organs.

The aforementioned limitations of systemic delivery would be obviated by local intramural delivery of the therapeutic agent directly to the vessel wall at the target site. Accordingly, interest has been shown in the development of catheters that can deliver medication directly to a target site within a blood vessel or other bodily lumen. Typically, such prior art drug delivery catheters include a balloon at the distal end of the catheter. The balloon is introduced into the vascular lumen and located adjacent the target site, at which time it is expanded to engage the lumen wall. The balloon is provided with a porous surface, such that the pressurized liquid that expands the balloon escapes through the pores to the luminal wall surface. Thus, the pressurized liquid that expands the balloon also serves as the vehicle for the therapeutic agent.

Drug delivery catheters of the perforated balloon type do, however, have some drawbacks. For example, because the same fluid is used as the balloon inflation medium and as the drug medium, dilatation by balloon expansion is necessarily accompanied by drug delivery; neither function can be performed independently, which may be disadvantageous or inefficient in various clinical situations. Further inefficiency is engendered by the expulsion of the therapeutic agent before the balloon is fully expanded, so that the agent is not as forcefully administered to the luminal wall tissue as it would be if the balloon were fully expanded so as to bring it into close proximity or contact with the wall. A related problem is that the agent is typically expelled at relatively low pressures that are insufficient to effect any substantial degree of penetration of the lumen wall surface, thereby limiting the therapeutic effect of the agent in certain situations. Finally, in drug delivery PTA catheters in which the same fluid is used as the balloon inflation medium and the drug medium, the reversal of fluid flow to deflate the balloon may tend to draw blood into the catheter, requiring the catheter to be withdrawn for purging or replacement after a single use.

Examples of the above-described "single fluid" perforated balloon type of drug delivery dilatation catheter are disclosed in the following U.S. Pat. No. 5,087,244—Wolinsky et al.; U.S. Pat. No. 5,112,305—Barath et al.; and U.S. Pat. No. 5,344,402—Crocker.

U.S. Pat. No. 5,370,614—Amundson et al. discloses a balloon angioplasty catheter, wherein the balloon is contained within a frangible sheath. The space between the balloon and the sheath is filled with a drug-containing viscous matrix. Expansion of the balloon within a vascular lumen causes the sheath to burst, releasing the viscous matrix into the lumen. This construction requires a therapeutic agent that can be manufactured in the form of a viscous matrix, which may not be possible or practical for all desired agents. Furthermore, the available dose of the agent is limited by the volume of the space between the balloon and the sheath, a volume that is further limited by the cross-sectional area of the lumen at the target site. As with more typical "single fluid" perforated balloon infusion catheters, dilatation and infusion cannot be performed independently.

U.S. Pat. No. 4,994,033—Shockey et al. discloses a drug delivery dilatation catheter, in which an imperforate dilatation balloon is concentrically surrounded by a second expansible membrane that is perforated. While an inflation fluid is delivered to the dilatation balloon, a therapeutic agent is introduced into the space between the dilatation balloon and the perforated membrane, thereby expanding both the dilatation balloon and the perforated membrane, the latter engaging the lumen wall. The agent is thereby forced out of the perforations to bathe the lumen wall tissue. Proper delivery of the agent requires a delivery pressure sufficient to expand the outer, perforated membrane. Furthermore, the outer membrane perforations must be minute ("microholes"). This device thus requires a specialized manufacturing step, e.g., precision laser drilling, thereby adding to its cost of manufacture.

Another approach is taken by the device described in U.S. Pat. No. 5,336,178—Kaplan et al. This device comprises a multi-lumen expansible sleeve that slides over the exterior of a standard PTA balloon catheter. The lumens of the sleeve are ported at their distal ends. Inflation of the balloon at the delivery site expands the sleeve to bring the delivery ports into close proximity with the surrounding tissue, whereupon a therapeutic agent is delivered to the tissue via the sleeve lumens and their ports. While this device allows dilatation and infusion to be performed independently, in the commercially available embodiment of this device, the dilatation must be performed first, the balloon deflated, the sleeve passed over the balloon, and the balloon then reinflated before infusion commences. This procedure can result in the movement of the dilatation catheter away from the target site, thus requiring laborious repositioning of the combined dilatation and infusion catheter assembly. In addition, the distribution of the agent in this device (as in the perforated balloon-type of devices) is limited by the size, distribution, and number of holes or ports through which the agent flows into the vessel. Furthermore, the use of a multi-lumen concentric sleeve over the balloon dictates a relatively large uninflated cross-sectional area for the device, even in those embodiments (as described in the aforementioned U.S. Pat. No. 5,336,178) that do not require the inflation-deflation-reinflation procedure. This makes the device disadvantageous for use in smaller blood vessels and bodily passages, and in those vessels and passages that have highly occlusive stenoses. In addition, the rather complex structure of this device may contribute to relatively high manufacturing costs.

There has thus been a need for a drug delivery dilatation catheter that permits dilatation and drug delivery (infusion) to be performed independently. Furthermore, the need has been felt for such a device that has an uninflated or unexpanded cross-sectional area that is not significantly greater than that of an ordinary balloon-type of PTA catheter. In addition, it would be advantageous for such a device to be capable of delivering the drug at pressures sufficient to penetrate the surface of the tissue surrounding the lumen into which the catheter is placed.

SUMMARY OF THE INVENTION

Broadly, the present invention is a drug delivery (infusion) catheter for use in conjunction with a dilatation catheter having an inflatable element (balloon) near its distal end that is inflated by an inflation fluid delivered via an inflation lumen. The infusion catheter of the present invention comprises an elongate, flexible tube defining an infusion lumen, and an expansible infusion sleeve located near the distal end of the infusion catheter, at the distal terminus of the infusion lumen, the sleeve comprising an expansible grid or network of spacer elements disposed between proximal and distal resilient sealing bands. When the present invention is employed with such a dilatation catheter, the balloon of the dilatation catheter is enclosed within the expansible infusion sleeve, whereby the spacer elements of the sleeve create a flow path or interstice between the balloon and the vessel wall that communicates with the infusion lumen through which a liquid therapeutic agent is delivered.

More specifically, the present invention is adapted for deployment with a balloon catheter comprising a first tube defining a first or inflation lumen, and an inflatable dilatation balloon near the distal end of the first tube, in fluid communication with the first lumen. When so deployed, the present invention comprises a second tube concentrically surrounding the first tube and defining a second or infusion lumen therebetween; and an infusion sleeve concentrically surrounding the balloon, wherein the sleeve comprises an expansible grid or network of spacer elements, with the proximal and distal ends of the sleeve attached to resilient elastomeric sealing bands. The spacer elements of the expansible grid or network create an axially-elongated, circumferential flow path or interstice between the balloon and the vessel wall when the balloon is inflated, the interstice being in fluid communication with the second lumen, through which the agent flows for penetration into the tissue of the vessel wall.

In a first preferred embodiment, the expansible grid of the infusion sleeve comprises a resiliently expansible network of filaments or strands that define a network of spacer elements, the network having a substantial degree of shape memory. The grid is permanently fixed to the proximal and distal sealing bands. In a second preferred embodiment, the grid comprises a perforated tube of deformable, biocompatible metal (e.g., stainless steel) formed as a mesh or latticework, whereby the tube defines a network of spacer elements. In this second embodiment, the grid is detachably joined to the proximal and distal sealing bands, so that it can be left at the treatment site as a stent.

In use, a catheter assembly comprising the present invention and a balloon dilatation catheter is first employed as a conventional balloon angioplasty catheter; that is, it is deployed so as to position the balloon at its distal end at the target site for treatment (e.g., a stenotic or atherosclerotic region of a blood vessel). The balloon is inflated by the introduction of an inflation fluid under pressure to the interior of the balloon through the first lumen, whereby the vascular obstruction is cleared as in conventional angioplasty. The infusion sleeve expands with the balloon, but does not significantly inhibit or interfere with the performance of the angioplasty function.

The next step is the infusion of a liquid therapeutic agent through the second lumen and into the tissues of the vessel through the interstice created by the spacer elements of the expansible grid. In performing this infusion step, the balloon may either remain inflated after it is used to clear the vascular obstruction, or it may be first deflated and then reinflated. In either case, the inflation of the balloon causes the infusion sleeve to expand radially outwardly until the spacer elements of the grid contact the vascular tissue, creating an axially elongated interstice between the balloon and the vessel wall, completely circumscribing the balloon. In addition, the expansion of the infusion sleeve displaces the proximal and distal sealing bands radially outwardly against the wall of the vessel, to assure that fluid directed into the interstice does not flow upstream or downstream therefrom, but, rather, is distributed at the target site. The interstice permits the infused agent to be expelled from the second lumen into the tissue under sufficient pressure to effect the penetration of the agent through the surface layers of the tissue, thereby achieving optimal therapeutic effect. The circumferential configuration of the interstice permits a 360 degree distribution of the agent throughout the target site.

In the first preferred embodiment, the balloon is deflated, and the shape memory of the network of spacer elements causes the infusion sleeve to contract with the balloon, permitting the catheter to be removed. In the second preferred embodiment, the metal mesh grid remains expanded and seated against the vessel wall after the balloon is deflated. The catheter is then displaced axially in the distal direction to detach the grid from the distal sealing band, which resiliently collapses radially inwardly against the catheter. Then, the catheter is withdrawn axially in the proximal direction to detach the grid from the proximal sealing band, which likewise collapses radially inwardly, allowing the catheter to be fully withdrawn. The grid remains in place, seated against the vessel wall, to function as a stent.

As compared with prior art infusion and dilatation catheters, the present invention offers a number of distinct advantages. First, since the therapeutic agent is not used as the inflation fluid, the dilatation function can be performed either with or without a subsequent infusion. This allows the repetition of the dilatation function, as is frequently necessary, before the infusion is performed, and it allows the infusion to be controllably performed when the balloon and sleeve are in their optimally inflated radial positions, thereby allowing the agent to be introduced to the tissue under sufficient pressure for optimal penetration. In addition, the infusion sleeve does not appreciably add to the cross-sectional area of the balloon, either in the latter's inflated or deflated states, thereby allowing the catheter to be used even in relatively narrow vessels. Furthermore, removal of the catheter is not necessary between the dilatation and infusion functions, thereby obviating the possible loss of position relative to the target site. Also, the even distribution of the interstices throughout the area of the mesh sleeve results in a corresponding even distribution of the agent throughout the target site. These advantages are achieved with a construction that requires manufacturing techniques that are neither costly nor complicated.

These advantages, as well as others, will be more fully appreciated from the detailed description below.

BRIEF DESCRIPTION OF THE DRAWINGS

FIGS. 1 and 2 are perspective views of a combined infusion and dilatation catheter assembly employing an infusion catheter in accordance with a first preferred embodiment of the present invention, showing how the infusion catheter of the present invention and a dilatation catheter are assembled with each other;

FIG. 3 is a semi-diagrammatic view, showing the deployment of the catheter assembly of FIG. 1, including the present invention, in a human patient;

FIG. 4 is a perspective view of the distal end of an infusion catheter in accordance with the first preferred embodiment of the present invention, as assembled with a dilatation catheter, partially broken away to reveal the structure of the infusion sleeve, the assembly being shown with its dilatation balloon positioned at a target site in a bodily passage or lumen and in its deflated state;

FIG. 5 is a view similar to that of FIG. 4, showing the balloon partially inflated;

FIG. 6 is a view similar to that of FIG. 4, showing the balloon in its fully inflated state;

FIG. 7 is a lateral cross-sectional view, taken along line 7—7 of FIG. 6;

FIG. 8 is a longitudinal cross-sectional view, taken along line 8—8 of FIG. 4;

FIG. 9 is a longitudinal cross-sectional view, taken along line 9—9 of FIG. 6;

FIG. 10 is a perspective view of a combined infusion and dilatation catheter assembly employing an infusion catheter in accordance with a second preferred embodiment of the present invention, showing the infusion sleeve in a collapsed state;

FIG. 11 is a view similar to that of FIG. 10, showing the infusion sleeve in an expanded state;

FIG. 12 is a cross-sectional view taken along line 12—12 of FIG. 10;

FIG. 13 is a cross-sectional view taken along line 13—13 of FIG. 11;

DETAILED DESCRIPTION OF THE PREFERRED EMBODIMENTS

Figure 14:
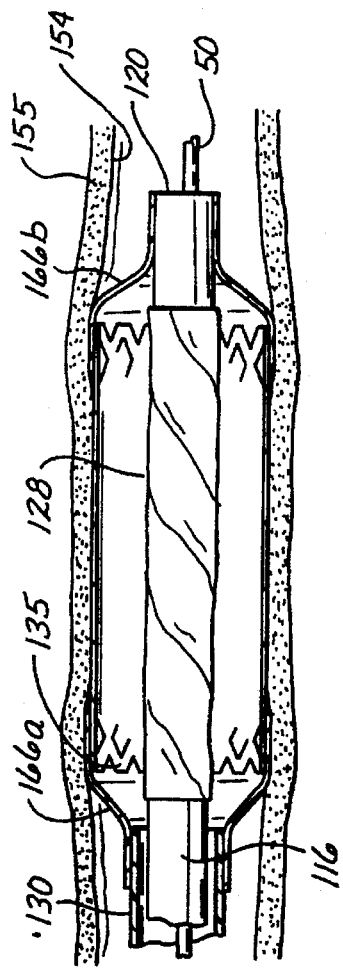
FIG. 14 is a detailed view of the distal end portion of the combined infusion and dilatation catheter assembly of FIG. 10, showing the infusion sleeve in its expanded state within the lumen of a blood vessel or other bodily passage.

FIGS. 1 and 2 show an infusion and dilatation catheter assembly 10, comprising a dilatation catheter subassembly 12 and an infusion catheter subassembly 14, the latter in accordance with a first preferred embodiment of the present invention. The dilatation catheter subassembly 12 is similar to conventional balloon dilatation catheters. It comprises an elongate, flexible, hollow inflation tube 16 having a proximal end 18 and a distal end 20. The proximal end 18 terminates in a coupling member 22, suitable for removable coupling to a pressurized inflation fluid source, as will be described below. A relatively short distance distally from its proximal end 18, the inflation tube 16 passes through a "Y"-fitting 24, inside of which it is joined by a guide wire tube 26, the latter having a distal end (not shown) that is fluidly connected to the inflation tube 16 inside the fitting 24.

The distal end 20 of the inflation tube 16 is open for the passage of a guide wire therethrough, as will be described below. Located a short distance proximally from the distal end 20 of the inflation tube 16 is a balloon 28, the interior of which is in fluid communication with the interior of the inflation tube 16, so that the balloon 28 is inflatable by an inflation fluid delivered to the interior of the inflation tube 16 through the coupling member 22, as will be described more fully below.

The infusion catheter subassembly 14 comprises an elongate, flexible, hollow infusion tube 30, having a main portion 31 with a proximal end 32, and a distal end portion 34, with an expansible infusion sleeve 35, to be described in detail below, coaxially connected therebetween. The distal end portion 34 of the infusion tube 30 terminates in a tapered, open distal tip 36 to receive the distal end 20 of the inflation tube 16, as will be described below.

The proximal end 32 of the infusion tube 30 terminates in a sealing plug 37 having a proximal side that is closed by a penetrable sealing element 38, such as a slit diaphragm, as shown. The interior of the sealing plug 37 provides fluid communication between the infusion tube 30 and an external infusion line 40, the distal end of which is connected to the sealing plug 37 near the proximal side of the sealing plug 37, just distally from the sealing element 38. The external infusion line 40 has a proximal end that terminates in a stopcock valve 42, having one or more inlet ports 44.

The infusion and dilatation catheter 10 is formed as an assembly of the dilatation catheter subassembly 12 and the infusion catheter subassembly 14. The distal end 20 of the inflation tube 16 of the dilatation catheter subassembly 12 is first inserted through the sealing element 38 and the sealing plug 37. Then, the inflation tube 16 is pushed transluminally through the infusion tube 30 of the infusion catheter subassembly 14, until the balloon 28 is approximately centered within the interior of the infusion sleeve 35, with the distal end 20 of the inflation tube 16 extending a short distance distally from the opening in the distal end portion 34 of the infusion tube 30.

FIG. 3 shows the dilatation and infusion catheter 10 as it would be set up and used for a typical PTA procedure on a human patient 48. A guide wire 50 is inserted into the patient 48 through an artery (not shown), accessed through a percutaneous puncture at the appropriate place in the patient's body. (In a typical PTA procedure, the artery would be the femoral artery, accessed percutaneously through the patient's groin, although it is understood that the present invention is not limited to such an application.) The guide wire 50 is fed through the patient until its distal portion reaches the coronary artery (not shown) in which the target site for treatment (e.g., the stenotic or atherosclerotic area) is located. The dilatation and infusion catheter 10 is then passed over the guide wire 50, so that the guide wire 50 extends transluminally through the inflation tube 16, until the balloon 28 and the infusion sleeve 35 are positioned at the target site. The guide wire 50 then extends into the interior of the guide wire tube 26 through the "Y"-fitting 24, the proximal end of the guide wire 50 extending out of the open proximal end of the guide wire tube 26. A source of pressurized inflation fluid, such as a syringe 52, is fluidly connected to the coupling member 22 for inflating the balloon, as will be described below.

FIGS. 4 through 9 illustrate the construction and operation of the balloon 28 and the infusion sleeve 35 within the lumen 54 of a blood vessel 55, such as a coronary artery, for example.

The interior of the inflation tube 16 is seen to define a first or inflation lumen 56 that is in fluid communication with the interior of the balloon 28 through an orifice 57. A second or infusion lumen 58 is defined between the interior wall surface of the infusion tube 30 and the exterior wall surface of the inflation tube 16. When the balloon 28 is deflated (FIGS. 4 and 8), the infusion sleeve 35 concentrically surrounds the balloon 28, and is spaced therefrom; this space is in fluid communication with the infusion lumen 58.

The infusion sleeve 35 is in the form of a resiliently expansible grid that comprises a network of filaments or strands 60 that define a resiliently expansible network of spacer elements. The strands or filaments 60 may be of any suitable cross-sectional shape, e.g., square, circular, triangular, or other. The strands or filaments 60, in turn, may be considered as defining a plurality of spacer elements, in a pattern of substantially even distribution throughout the area of the sleeve 35. The strands or filaments 60 are shown as forming a crisscross pattern in the drawings, but other patterns may be found that will function adequately. For example, the expansible grid section of the infusion sleeve 35 may comprise filaments in a radial pattern, a longitudinal pattern, a spiral pattern, or a combination of patterns. The filaments or strands 60 may be formed of any suitable biocompatible, nonelastomeric, polymeric material, in monofilament form, with polyester being preferred.

The infusion sleeve 35 has a proximal end 62 and a distal end 64. It is sealed at its proximal end 62 to the distal end of the main portion 31 of the infusion tube 30, and at its distal end 64 to the proximal end of the distal end portion 34 of the infusion tube 30. The sealing may be effected by a biocompatible adhesive, by thermal bonding, or by ultrasonic sealing, as is well known in the art. Permanently fixed to each of the sealed ends 62, 64 and the portions of the infusion sleeve 35 immediately adjacent thereto is a sealing band 66 that covers the infusion sleeve 35 so as to make it fluid tight in those areas. Alternatively, the sealing bands 66 may be applied so as to provide the sealing between the sleeve end portions 62, 64 and the infusion tube 30. The sealing bands 66 may be formed of any of several suitable biocompatible elastomeric materials, such as, for example, elastomeric silicone, polyurethane, latex, and various thermoplastic elastomers well-known in the pertinent arts.

As shown in FIGS. 4 and 8, the infusion sleeve 35 has a relaxed or contracted state or position in which its outside diameter is approximately equal to that of the infusion tube 30. This relaxed position is assumed when the balloon 28 is deflated. In the relaxed position of the sleeve 35, the spacing between the expansible filaments 60 of the sleeve 35 is at its minimum. The filaments 60 are, however, sufficiently spaced apart to allow the flow of fluid therethrough from the infusion lumen 58 to the interior of the bodily passage 54.

As illustrated in FIGS. 5, 6, 7, and 9, the inflation of the balloon 28 causes the radial expansion of the infusion sleeve 35, thereby increasing the spacing between the expansible filaments 60. Furthermore, as best shown in FIG. 9, in the expanded position or state of the infusion sleeve 35, the filaments 60 of the sleeve 35 are brought into contact with the tissue of the vessel 55, the filaments 60 thereby functioning as a network of spacer elements that create an axially-elongated interstice 68 between the balloon 28 and the interior wall surface of the vessel. The interstice 68 defines a fluid flow path that circumferentially surrounds the balloon 28 a full 360 degrees. At the same time, the sealing bands 66 are displaced radially outwardly to provide fluid-tight seals between the balloon 28 and the portions of the vessel wall immediately upstream (proximally) and downstream (distally) from the interstice 68 created by the sleeve filaments 60, whereby fluid infused through the infusion lumen 58 is directed into the interstice 68, as described below.

In use, for example, in a PTA procedure, the above-described embodiment of the present invention is first deployed, as described above, in the manner of a conventional balloon angioplasty catheter. When the balloon 28 and the infusion sleeve 35 are positioned at the target site, the balloon 28 is inflated, in the manner described above, to perform the angioplasty function. As is typical in such procedures, the balloon 28 may be successively inflated, deflated, and reinflated two or more times before the desired results of the procedure are achieved.

If it is desired to apply a therapeutic agent to the tissues of the vessel, infusion of the agent is advantageously performed while the balloon 28 is inflated and the infusion sleeve 35 is in its expanded state, with its filaments 60 in contact with the vessel wall, as explained above. With the stopcock valve 42 in the external infusion line 40 open, the agent is introduced into one of the inlet ports 44 of the valve 42, from which it flows through the external infusion line 40, through the sealing plug 37, and then through the infusion lumen 58 defined within the infusion tube 30, as described above. Upon exiting the distal end of the infusion lumen 58 and flowing past the proximal sealing band 66, the agent is expressed out of the sleeve 35 and over the outside surface of the balloon 28 into the interstice 68. If the agent is infused at a relatively low pressure, it will bathe the tissue of the vessel wall. If it is infused at higher pressures, it will be expressed into the interstice 68 with sufficient pressure to penetrate beneath the superficial surface tissues of the vessel wall. In either case, the agent will be substantially evenly dispersed in a 360 degree distribution around the vessel wall, for optimum therapeutic effect.

Upon completion of the infusion, the balloon 28 is deflated. The shape memory of the infusion sleeve 35 cause it to collapse substantially to its original contracted state substantially simultaneously with the deflation of the balloon 28, while the resilient sealing bands 66 likewise collapse radially inwardly, thereby allowing the catheter assembly 10 to be withdrawn.

Alternatively, infusion can be performed while the balloon 28 is partially or fully deflated. The spaces defined between the strands or filaments 60 are open to a sufficient degree to permit the passage of the agent, even when the infusion sleeve 35 is in its contracted state.

Of course, the catheter 10 can also be used when dilatation without infusion is desired, since the infusion sleeve 35 does not significantly affect the dilatation function.

It will be appreciated that the dilatation and infusion catheter 10 of the present invention can be employed for procedures within blood vessels other than the coronary arteries, and within other bodily passages, such as the biliary ducts and the lumens of the genito-urinary organs, including, but not limited to, the urethra. The variations in the method of use of the catheter 10 for such other procedures will naturally suggest themselves to the skilled practitioner.

Furthermore, it will be apparent that the infusion catheter subassembly 14 of the present invention can be employed with a wide variety of balloon type dilatation catheters as the aforementioned dilatation catheter subassembly 12. Thus, in its broader aspect, the present invention comprises the infusion catheter subassembly 14 and its method of use; in another aspect, the present invention may be seen to comprise the infusion and dilatation catheter assembly 10 and its method of use.

A second preferred embodiment of the present invention is illustrated in FIGS. 10 through 16. This embodiment, as will be described below, differs from the previously described embodiment principally in the structure and function of the infusion sleeve.

Referring now to FIGS. 10 and 11, an infusion and dilatation catheter assembly 110, in accordance with the second preferred embodiment, is seen to comprise a dilatation catheter subassembly 112 and an infusion catheter assembly 114, assembled in the manner described above in connection with the first embodiment.

As in the first embodiment, the dilatation catheter subassembly 112 is similar to conventional balloon dilatation catheters. It comprises an elongate, flexible, hollow inflation tube 116 having a proximal end 118 and a distal end 120. The proximal end 118 terminates in a coupling member 122, suitable for removable coupling to a pressurized inflation fluid source, as described above. A relatively short distance distally from its proximal end 118, the inflation tube 116 passes through a "Y"-fitting 124, inside of which it is joined by a guide wire insertion tube 126, the latter having a distal end (not shown) that is fluidly connected to the inflation tube 116 inside the fitting 124.

The distal end 120 of the inflation tube 116 is open for the passage of a guide wire therethrough, as described above. Located a short distance proximally from the distal end 120 of the inflation tube 116 is a balloon 128, the interior of which is in fluid communication with the interior of the inflation tube 116, so that the balloon 128 is inflatable by an inflation fluid delivered to the interior of the inflation tube 116 through the coupling member 122, as will be described more fully below.

The infusion catheter subassembly 114 comprises an elongate, flexible, hollow infusion tube 130, having a proximal end 132, and a distal end 134. The distal end 120 of the inflation tube 116 extends distally past the distal end 134 of the infusion tube 130 when the inflation tube 116 is inserted transluminally through the infusion tube 130 to form the catheter assembly 110. Detachably joined coaxially between the distal end 134 of the infusion tube 130 and the distal end 120 of the inflation tube 116, in the manner to be described below, is an expansible infusion sleeve 135, which will be described in detail below.

The proximal end 132 of the infusion tube 130 terminates in a sealing plug 137 having a proximal side that is closed by a penetrable sealing element 138, such as a slit diaphragm, as shown. The interior of the sealing plug 137 provides fluid communication between the infusion tube 130 and an external infusion line 140, the distal end of which is connected to the sealing plug 137 near the proximal side of the sealing plug 137, just distally from the sealing element 138. The external infusion line 140 has a proximal end that terminates in a stopcock valve 142, having one or more inlet ports 144.

The infusion sleeve 135 of the second embodiment comprises a grid in the form of a perforated tube of deformable, biocompatible metal (e.g., stainless steel) formed as a mesh or latticework, whereby the tube defines an expansible network of spacer elements 160, as will be described below. The proximal end of the infusion sleeve 135 is detachably joined to a proximal sealing band 166a, which, in turn, is fluid-tightly sealed to the distal end 134 of the infusion tube 130. The distal end of the infusion tube 135 is detachably joined to a distal sealing band 166b, which, in turn, is fluid-tightly sealed to the distal end 120 of the inflation tube 116.

FIGS. 12 through 16 illustrate the operation of the second embodiment of the invention within the lumen 154 of a bodily vessel, passage, or duct 155, which may be, for example, a coronary artery, the urethra, or the bile duct.

The interior of the inflation tube 116 is seen to define a first or inflation lumen 156 that is in fluid communication with the interior of the balloon 128 through an orifice 157. A second or infusion lumen 158 is defined between the interior wall surface of the infusion tube 130 and the exterior wall surface of the inflation tube 116. When the balloon 128 is deflated (FIG. 12), the infusion sleeve 135 concentrically surrounds the balloon 128, and is spaced therefrom; this space is in fluid communication with the infusion lumen 158.

As shown in FIG. 12, the infusion sleeve 135 has a relaxed or contracted state or position in which its outside diameter is approximately equal to that of the infusion tube 130. This relaxed position is assumed when the balloon 128 is deflated. In the relaxed position of the sleeve 135, the spacing between the spacer elements 160 of the expansible grid of the sleeve 135 is at its minimum. The spacer elements 160 are, however, sufficiently spaced apart to allow the flow of fluid therethrough from the infusion lumen 158 to the interior of the bodily passage 154.

As illustrated in FIG. 13, the balloon 128 has been inflated by the introduction of an inflation fluid through the inflation lumen 156, and then through the orifice 157 into the interior of the balloon 128. The inflation of the balloon 128 causes the radial expansion of the infusion sleeve 135, thereby expanding the grid so as to increase the spacing between the spacer elements 160. Furthermore, in the expanded position or state of the infusion sleeve 135, the spacer elements 160 of the sleeve 135 are brought into contact with the tissue of the vessel 155, the spacer elements 160 thereby creating an axially-elongated interstice 168 between the balloon 128 and the interior wall surface of the vessel or passage 155. The interstice 168 defines a fluid flow path that circumferentially surrounds the balloon 128 a full 360 degrees. At the same time, the sealing bands 166a, 166b are displaced radially outwardly to provide fluid-tight seals between the balloon 128 and the portions of the vessel or passage wall immediately upstream (proximally) and downstream (distally) from the interstice 168 created by the spacer elements 160, whereby fluid infused through the infusion lumen 158 is directed into the interstice 168, as described below.

In use, the second embodiment of the present invention is first deployed, as described above, in the manner of a conventional balloon catheter. When the balloon 128 and the infusion sleeve 135 are positioned at the target site, the balloon 128 is inflated, as described above.

Infusion of a therapeutic agent is advantageously performed while the balloon 128 is inflated and the infusion sleeve 135 is in its expanded state, with its spacer elements 160 in contact with the vessel or passage wall, as explained above. With the stopcock valve 142 in the external infusion line 140 open, the agent is introduced into one of the inlet ports 144 of the valve 142, from which it flows through the external infusion line 140, through the sealing plug 137, and then through the infusion lumen 158 defined within the infusion tube 130, as described above. Upon exiting the distal end of the infusion lumen 158 and flowing past the proximal sealing band 166a, the agent is expressed out of the sleeve 135 and over the outside surface of the balloon 128 into the interstice 168. If the agent is infused at a relatively low pressure, it will bathe the tissue of the vessel or passage wall. If it is infused at higher pressures, it will be expressed into the interstice 168 with sufficient pressure to penetrate beneath the superficial surface tissues of the vessel or wall. In either case, the agent will be substantially evenly dispersed in a 360 degree distribution around the vessel or passage wall, for optimum therapeutic effect.

Alternatively, as in the first embodiment, infusion can be performed while the balloon 128 is partially or fully deflated. The spaces defined between the spacer elements 160 are open to a sufficient degree to permit the passage of the agent, even when the infusion sleeve 135 is in its contracted state.

Figure 15:
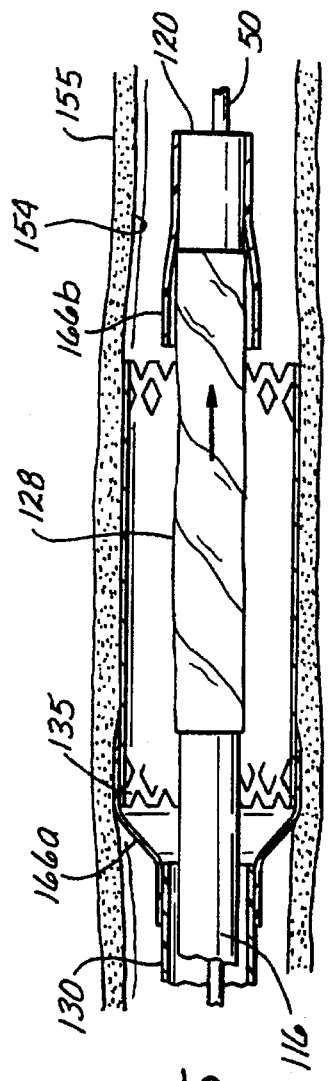
FIG. 15 is a view similar to that of FIG. 14, showing the expansible grid of the infusion sleeve being separated from the distal sealing band of the infusion sleeve.
Figure 16:
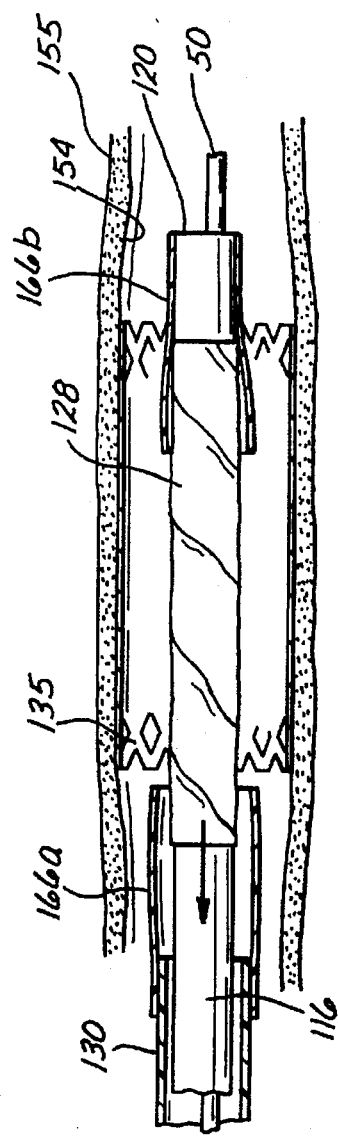
FIG. 16 is a view similar to that of FIGS. 14 and 15, showing the expansible grid of the infusion sleeve being separated from the proximal sealing band of the infusion sleeve.

As illustrated in FIGS. 14, 15, and 16, the infusion sleeve 135 of the second embodiment of the invention is designed to be left in place as a stent after the withdrawal of the catheter assembly 110. As shown in FIG. 14, after the balloon 128 is deflated, the infusion sleeve 135 remains expanded and seated against the interior wall of the vessel or passage 155. The process of removing the catheter assembly while leaving the infusion sleeve 135 in place is begun, as shown in FIG. 15, by displacing the dilatation catheter subassembly 112 axially forwardly. The frictional engagement between the infusion sleeve 135 and the surrounding tissue causes it to remain in place, thereby causing the distal sealing band 166b to be detached from the distal end of the infusion sleeve 135, whereupon the distal sealing band 166b collapses radially inwardly toward the dilatation catheter 116.

Finally, as shown in FIG. 16, the entire catheter assembly 110 is withdrawn axially, in the proximal direction, causing the proximal sealing band 166a to be detached from the proximal end of the infusion sleeve 135. The infusion sleeve is the left in place within the vessel or passage 155, functioning as a stent.

If desired, the infusion sleeve 135 may be pretreated with a therapeutic agent, so that, while functioning as a stent, it also maintains prolonged contact of the agent with the tissue. Furthermore, the prior infusion process may leave a residue of the agent on the infusion sleeve 135, thereby prolonging the therapeutic effect after the sleeve 135 is left behind as a stent.

While two preferred embodiments of the invention have been described herein, a number of variations and modifications may suggest themselves to those skilled in the pertinent arts, especially, as mentioned above, in connection with the employment of the present invention in bodily passages other than the coronary arteries. Such modifications and variations should be considered within the spirit and scope of the invention, as defined in the claims that follow.

What is claimed is:

1. An infusion and dilatation device for insertion into a vessel, duct, or passage in the body of a patient, comprising:

a dilatation catheter having an elongate, flexible catheter tube defining an inflation lumen in fluid communication with an inflatable element near the distal end of the catheter tube, and wherein the inflatable element is inflatable from a deflated state to an inflated state by a pressurized inflation fluid received from the inflation lumen;

an elongate, flexible infusion tube internally dimensioned so as to allow the catheter tube to be disposed concentrically therein, and having a distal end; and an expansible sleeve, on the infusion tube near the distal end thereof, that assumes a contracted position when the inflatable element is in the deflated state and an expanded position when the inflatable element is in the inflated state, the sleeve comprising a perforated tubular element defining a deformable expansible network of spacer elements, wherein the sleeve is permanently deformable to its expanded position;

whereby, when the catheter tube is disposed within the infusion tube, (a) an infusion lumen is defined between the catheter tube and the infusion tube, (b) the infusion lumen has a distal end proximal to the sleeve, and (c) the sleeve concentrically surrounds the inflatable element so as to be deformable into an expanded position by the inflation of the inflatable element; and whereby the spacer elements create an interstice between the inflatable element and a surrounding interior tissue surface of the vessel, duct, or passage for fluid flow axially from the distal end of the infusion lumen to the interstice and thereby to the interior tissue surface around the inflatable element when the sleeve is in its expanded position.

2. The device of claim 1, wherein the outside diameter of the sleeve is approximately equal to the outside diameter of the infusion tube when the sleeve is in the contracted position.

3. The device of claim 1, wherein the spacing between the spacer elements is at a minimum when the sleeve is in its contracted position, and at a maximum when the sleeve is in its expanded position, the minimum spacing being sufficient to permit the passage of a liquid therapeutic agent therethrough.

4. The device of claim 1, wherein a portion of the catheter tube extends distally through the distal end of the infusion tube, and wherein the sleeve is coaxially attached between the distal end of the infusion tube and the distally extended portion of the catheter tube.

5. The device of claim 4, wherein the sleeve is joined to the distal end of the infusion tube by an elastomeric proximal sealing element and to the distally extended portion of the catheter tube by an elastomeric distal sealing element, the proximal and distal sealing elements being displaceable radially outwardly when the sleeve is moved from its contracted position to its expanded position.

6. The device of claim 5, wherein the sleeve is detachably joined to the proximal and distal sealing elements.

7. An infusion and dilatation device for insertion into a vessel, duct, or passage in the body of a patient, comprising:

a dilatation catheter having an elongate, flexible catheter tube defining an inflation lumen in fluid communication with an inflatable element near the distal end of the catheter tube, and wherein the inflatable element is inflatable from a deflated state to an inflated state by a pressurized inflation fluid received from the inflation lumen;

an elongate, flexible infusion tube internally dimensioned so as to allow the catheter tube to be disposed concentrically therein, and having a distal end; and an expansible sleeve, on the infusion tube near the distal end thereof, and comprising an expansible network of spacer elements, wherein the sleeve assumes a contracted position when the inflatable element is in the deflated state and an expanded position when the inflatable element is in the inflated state, and wherein the sleeve is connected to the infusion tube by an elastomeric sealing element that is displaceable radially outwardly when the sleeve is moved from its contracted position to its expanded position;

whereby, when the catheter tube is disposed within the infusion tube, (a) an infusion lumen is defined between the catheter tube and the infusion tube, (b) the infusion lumen has a distal end proximal to the sleeve, and (c) the sleeve concentrically surrounds the inflatable element so as to be deformable into an expanded position by the inflation of the inflatable element; and whereby the spacer elements create an interstice between the inflatable element and a surrounding interior tissue surface of the vessel, duct, or passage for fluid flow axially from the distal end of the infusion lumen to the interstice and thereby to the interior tissue surface around the inflatable element when the sleeve is in its expanded position.

8. The device of claim 7, wherein the outside diameter of the sleeve is approximately equal to the outside diameter of the infusion tube when the sleeve is in the contracted position.

9. The device of claim 7, wherein the spacing between the spacer elements is at a minimum when the sleeve is in its contracted position, and at a maximum when the sleeve is in its expanded position, the minimum spacing being sufficient to permit the passage of a liquid therapeutic agent therethrough.

10. An infusion and dilatation device for insertion into a vessel, duct, or passage in the body of a patient, comprising:

a dilatation catheter having an elongate, flexible catheter tube defining an inflation lumen in fluid communication with an inflatable element near the distal end of the catheter tube, and wherein the inflatable element is inflatable from a deflated state to an inflated state by a pressurized inflation fluid received from the inflation lumen;

an elongate, flexible infusion tube internally dimensioned so as to allow the catheter tube to be disposed concentrically therein, and having a main tube portion and a distal end portion; and an expansible sleeve attached coaxially to the infusion tube between the main tube portion and the distal end portion thereof, and that assumes a contracted position when the inflatable element is in the deflated state and an expanded position when the inflatable element is in the inflated state, the sleeve comprising a resiliently expansible network of spacer elements, whereby the sleeve has sufficient shape memory to return substantially to its contracted position after having been expanded to its expanded position;

wherein the sleeve is joined to the main tube portion by an elastomeric proximal sealing element and to the distal end portion by an elastomeric distal sealing element, the proximal and distal sealing elements being displaceable radially outwardly when the sleeve is moved from its contracted position to its expanded position;

whereby, when the catheter tube is disposed within the infusion tube, (a) an infusion lumen is defined between the catheter tube and the infusion tube, (b) the infusion lumen has a distal end proximal to the sleeve, and (c) the sleeve concentrically surrounds the inflatable element so as to be deformable into an expanded position by the inflation of the inflatable element; and whereby the spacer elements create an interstice between the inflatable element and a surrounding interior tissue surface of the vessel, duct, or passage for fluid flow axially from the distal end of the infusion lumen to the interstice and thereby to the interior tissue surface around the inflatable element when the sleeve is in its expanded position.

11. The device of claim 10, wherein the outside diameter of the sleeve is approximately equal to the outside diameter of the infusion tube when the sleeve is in the contracted position.

12. The device of claim 10, wherein the spacing between the spacer elements is at a minimum when the sleeve is in its contracted position, and at a maximum when the sleeve is in its expanded position, the minimum spacing being sufficient to permit the passage of a liquid therapeutic agent therethrough.

13. The device of claim 10, wherein the sleeve is permanently fixed to the proximal and distal sealing elements.

14. A dilatation and infusion device for insertion into a vessel, passage, or duct in the body of a patient, comprising:

a first elongate, flexible, hollow tube having a proximal end, a distal end, and an inflation lumen;

an inflatable element near the distal end of the first tube and in fluid communication with the inflation lumen so as to be inflatable from a deflated state to an inflated state by an inflation fluid received from the inflation lumen;

a second elongate, flexible, hollow tube concentrically disposed around the first tube so as to define an infusion lumen between the first and second tubes, the second tube comprising a main tube portion and a distal end portion, the infusion lumen having a distal end terminating in the main tube portion;

an expansible sleeve coaxially connected between the main tube portion and the distal end portion of the second tube, in fluid communication with the distal end of the infusion lumen, and concentrically surrounding the inflatable element so as to be expansible to an expanded position in response to the inflation of the inflatable element, the sleeve comprising an expansible network of spacer elements defining an interstice between the inflatable element and an interior tissue surface of the vessel, passage, or duct when it is in its expanded position, thereby providing an axial fluid flow path from the distal end of the infusion lumen to the interstice and thereby to the interior tissue surface around the exterior of the inflatable element, wherein the sleeve assumes a contracted position, having an outside diameter that is approximately equal to the outside diameter of the main tube portion of the second tube, when the inflatable element is in the deflated state, and an expanded position when the inflatable element is in the inflated state; and elastomeric proximal and distal sealing elements respectively joining the sleeve to the main tube portion and the distal end tube portion, the proximal and distal sealing elements being displaceable radially outwardly when the sleeve is moved from its contracted position to its expanded position.

15. The device of claim 14, wherein the sleeve is permanently fixed to the proximal and distal sealing elements.

16. A dilatation and infusion device, comprising:

a first elongate, flexible, hollow tube having a proximal end and a distal end and having an inflation lumen;

an inflatable element near the distal end of the first tube and in fluid communication with the inflation lumen so as to be inflatable from a deflated state to an inflated state by a pressurized inflation fluid received from the inflation lumen;

a second, elongate, flexible, hollow tube concentrically disposed around the first tube so as to define an infusion lumen between the first and second tubes, and having a distal end through which a portion of the first tube extends distally; and an expansible sleeve, coaxially connected between the distal end of the second tube and the distally extended portion of the first tube, in fluid communication with the infusion lumen, and located so as to concentrically surround the inflatable element, the sleeve comprising an expansible network of spacer elements defining a flow path from the infusion lumen around the exterior of the inflatable element.

17. The device of claim 16, wherein the sleeve assumes a contracted position, having an outside diameter that is approximately equal to the outside diameter of the main tube portion of the second tube, when the inflatable element is in the deflated state, and an expanded position when the inflatable element is in the inflated state.

18. The device of claim 17, wherein the spacing between the spacer elements is at a minimum when the sleeve is in its contracted position, and at a maximum when the sleeve is in its expanded position, the minimum spacing being sufficient to permit the passage of a liquid therapeutic agent therethrough.

19. The device of claim 17, wherein the sleeve comprises a perforated tubular element defining a deformably expansible network of spacer elements, wherein the sleeve is permanently deformable to its expanded position.

20. The device of claim 19, wherein the sleeve is joined to the distal end of the second tube by an elastomeric proximal sealing element and to the distally extended portion of the first tube by an elastomeric distal sealing element, the proximal and distal sealing elements being displaceable radially outwardly when the sleeve is moved from its contracted position to its expanded position.

21. The device of claim 20, wherein the sleeve is detachably joined to the proximal and distal sealing elements.

22. A method of delivering a liquid therapeutic agent to a treatment site in the tissue surrounding a bodily passage, vessel, or duct, comprising the steps of:

providing a catheter assembly having an inflation lumen communicating with an inflatable element near its distal end, and an infusion lumen having a distal end communicating with an expansible infusion member located distally from the distal end of the infusion lumen, defining an expansible network of spacer elements, concentrically surrounding the inflatable element;

positioning the catheter assembly within the bodily passage, vessel, or duct so that the inflatable element and the infusion member are located at the treatment site;

inflating the inflatable element from a deflated state to an inflated state with an inflation fluid introduced through the inflation lumen to expand the infusion member radially from a contracted position to an expanded position in which the spacer elements are brought into contact with the treatment site, thereby creating an interstice between the inflatable element and the treatment site;

infusing the liquid agent into the treatment site while the inflatable element is inflated by expressing the liquid agent from the distal end of the infusion lumen into the interstice created by the spacer elements between the inflatable element and the treatment site;

deflating the inflatable element after the infusion step without restoring the infusion member to its contracted position;

detaching the infusion member from the catheter assembly while the spacer elements are in contact with the treatment site; and withdrawing the catheter assembly from the vessel, passage, or duct, leaving the infusion member in place at the treatment site as a stent.

23. The method of claim 22, wherein the spacing between the spacer elements is at a minimum when the infusion member is in its contracted position, and at a maximum when the infusion member is in its expanded position, the minimum spacing being sufficient to permit the passage of a liquid therapeutic agent therethrough.

24. The method of claim 22, wherein the step of infusing is performed at a pressure sufficient to allow the liquid agent to penetrate the surface of the tissue.

25. A method of delivering a liquid therapeutic agent to a treatment site in the tissue surrounding a bodily passage, vessel, or duct, comprising the steps of:

providing a catheter assembly having an inflation lumen fluidly communicating with an inflatable element near its distal end, and an infusion lumen having a distal end fluidly communicating with an expansible infusion member, located distally from the distal end of the infusion lumen, that defines an expansible network of spacer elements, concentrically surrounding the inflatable element;

positioning the catheter assembly within the bodily passage, vessel, or duct so that the inflatable element and the infusion member are located at the treatment site;

inflating the inflatable element from a deflated state to an inflated state with an inflation fluid delivered through the inflation lumen to expand the infusion member radially from a contracted position to an expanded position in which the spacer elements are brought into contact the treatment site and create an interstice between the inflatable element and the treatment site;

while the inflatable element is inflated and the spacer elements are in contact with the treatment site, delivering a liquid therapeutic agent from the distal end of the infusion lumen to the treatment site through the interstice;

deflating the inflatable element after the infusion step without restoring the infusion member to its contracted position;

detaching the infusion member from the catheter assembly while the spacer elements are in contact with the treatment site; and withdrawing the catheter assembly from the vessel, passage, or duct, leaving the infusion member in place at the treatment site as a stent.

26. The method of claim 25, wherein the spacing between the spacer elements is at a minimum when the infusion member is in its contracted position, and at a maximum when the infusion member is in its expanded position, the minimum spacing being sufficient to permit the passage of a liquid therapeutic agent therethrough.

27. The method of claim 25, wherein the step of infusing is performed at a pressure sufficient to allow the liquid agent to penetrate the surface of the tissue.

* * * * *